United States Patent
Samuelsson

(10) Patent No.: US 9,987,174 B2
(45) Date of Patent: Jun. 5, 2018

(54) ABSORBENT ARTICLE COMPRISING MORE THAN ONE STACKED ABSORBENT PAD

(71) Applicant: SCA Hygiene Products AB, Göteborg (SE)

(72) Inventor: Ann Samuelsson, Göteborg (SE)

(73) Assignee: SCA HYGIENE PRODUCTS AB, Göteborg (SE)

(*) Notice: Subject to any disclaimer, the term of this patent is extended or adjusted under 35 U.S.C. 154(b) by 127 days.

(21) Appl. No.: 15/034,288

(22) PCT Filed: Nov. 6, 2013

(86) PCT No.: PCT/SE2013/051302
§ 371 (c)(1),
(2) Date: May 4, 2016

(87) PCT Pub. No.: WO2015/069155
PCT Pub. Date: May 14, 2015

(65) Prior Publication Data
US 2016/0296385 A1    Oct. 13, 2016

(51) Int. Cl.
*A61F 13/15*    (2006.01)
*A61F 13/505*   (2006.01)
(Continued)

(52) U.S. Cl.
CPC ...... *A61F 13/505* (2013.01); *A61F 13/15699* (2013.01); *A61F 13/15707* (2013.01);
(Continued)

(58) Field of Classification Search
CPC .......... A61F 13/15699; A61F 13/15707; A61F 13/15739; A61F 13/15747; A61F 13/472;
(Continued)

(56) References Cited

U.S. PATENT DOCUMENTS 2,929,379 A * 3/1960 Poulsen ............... A61F 13/474
                                                    604/372
4,576,597 A * 3/1986 Hlaban ............. A61F 13/55145
                                                  604/385.21
(Continued)

FOREIGN PATENT DOCUMENTS

EP    0 788 785 A1    8/1997
WO    WO-95/29655 A1  11/1995
(Continued)

OTHER PUBLICATIONS

Extended European search report dated May 11, 2017 issued in corresponding European patent application No. 13897003.3 (7 pages).
(Continued)

*Primary Examiner* — Lynne Anderson
(74) *Attorney, Agent, or Firm* — Drinker Biddle & Reath LLP

(57) ABSTRACT

An absorbent article including at least two stacked absorbent pads which are releasably attached to each other, one being a first, user facing, absorbent pad and another being a second, garment facing, absorbent pad. The absorbent pads each have a liquid permeable topsheet; a backsheet; a first and second end region and a central region in the longitudinal direction; first and second lateral margins; and first and second transverse margins. The first and second absorbent pads are releasably attached to each other by joints along at least part of the respective first and second lateral margins in at least one of said end regions. The first and second absorbent pads are furthermore unattached from each other in an unattached region along at least a part of the transverse margins in the end region including the joints along the lateral margins. The first absorbent pad has a greater width, (Continued)

at least between the joints along the lateral margins in the end region, than the second absorbent pad.

20 Claims, 5 Drawing Sheets

(51) Int. Cl.
    *A61F 13/472*     (2006.01)
    *A61F 13/474*     (2006.01)
    *A61F 13/47*     (2006.01)

(52) U.S. Cl.
    CPC .......... *A61F 13/472* (2013.01); *A61F 13/474* (2013.01); *A61F 2013/4708* (2013.01)

(58) Field of Classification Search
    CPC .... A61F 13/474; A61F 13/505; A61F 13/515; A61F 2013/4708; A61F 2013/5055; A61F 13/47218; A61F 13/47227
    See application file for complete search history.

(56) References Cited

U.S. PATENT DOCUMENTS

| | | | | |
|---|---|---|---|---|
| 5,599,339 | A * | 2/1997 | Horney | A61F 13/474 604/387 |
| 5,843,254 | A | 12/1998 | Clark | |
| 5,910,137 | A * | 6/1999 | Clark | A61F 13/505 604/385.04 |
| 6,013,064 | A * | 1/2000 | Yamada | A61F 13/474 604/385.01 |
| 6,171,425 | B1 * | 1/2001 | Nukina | A61F 13/474 156/182 |
| 6,280,427 | B1 * | 8/2001 | Maggiulli | A61F 13/474 604/385.01 |
| 6,443,932 | B1 | 9/2002 | Maggiulli | |
| 8,303,557 | B2 * | 11/2012 | Ito | A61F 13/474 604/385.01 |
| 8,535,468 | B2 * | 9/2013 | Konthieng | A61F 13/15723 156/199 |
| 2004/0147894 | A1 * | 7/2004 | Mizutani | A61F 13/505 604/385.17 |
| 2006/0247590 | A1 | 11/2006 | Ito et al. | |
| 2009/0287171 | A1 | 11/2009 | Ito et al. | |
| 2011/0264068 | A1 | 10/2011 | Suga | |
| 2011/0319854 | A1 | 12/2011 | Suga et al. | |
| 2012/0310202 | A1 | 12/2012 | Wilson | |

FOREIGN PATENT DOCUMENTS

| | | |
|---|---|---|
| WO | WO-98/17220 A1 | 4/1998 |
| WO | WO-2006/025781 A1 | 3/2006 |

OTHER PUBLICATIONS

First Mexican Office Action No. Folio 94160 dated Dec. 4, 2017 issued in corresponding Mexican patent application No. MX/a/2016/005850 (5 pages) and its partial English-language translation thereof (7 pages).

* cited by examiner

ABSORBENT ARTICLE COMPRISING MORE THAN ONE STACKED ABSORBENT PAD

CROSS-REFERENCE TO PRIOR APPLICATION

This application is a § 371 National Stage Application of PCT International Application No. PCT/SE2013/051302 filed Nov. 6, 2013, which is incorporated herein in its entirety.

TECHNICAL FIELD

The present disclosure is generally related to disposable absorbent articles and, more particularly to absorbent articles made up of more than one stacked absorbent pad. The disclosure also provides for methods of producing such absorbent articles.

BACKGROUND

Disposable feminine absorbent articles, or feminine pads, are used by women during their menstrual cycles. Women also use these feminine absorbent articles as an everyday pantyliner in order to provide a feeling of freshness or dryness throughout the day. These absorbent articles must continuously be replaced during the day with a new absorbent article in order to prevent leakage and to ensure that the wearer at all times senses a high level of freshness and dryness. Discretion in the use of these products is also an aim for both the manufacturers and the users. Women are not at all occasions at their home or otherwise conveniently near a supply of absorbent articles, and it may be necessary to carry along a small supply of absorbent articles. Thus, feminine absorbent articles have been designed to be carried conveniently in a pocket or in a woman's handbag. However, an even more discreet way of carrying along the feminine absorbent articles is by using absorbent articles made up of more than one stacked absorbent pad which are releasably attached to each other and which conveniently allows the user to remove and to dispose the topmost feminine absorbent pad when needed and to reveal a clean and fresh absorbent pad underneath.

The stacked feminine absorbent pads are attached to each other, for example, by adhesive or by embossing. The attachment between the stacked absorbent pads may be provided only along the edges or throughout the entire backsheet of the overlaying articles. The stacked absorbent pads should adhere sufficiently to each other, so that the pads stay in place and not detach from each other, causing inconvenience or discomfort to the wearer. The adherence between the first and second absorbent pads should also not be too strong, rendering the removal of the first absorbent pad from the underlying absorbent pad difficult. Different solutions have previously been presented to facilitate the successive removal of the stacked absorbent pads.

U.S. Pat. No. 6,443,932 discloses a multi-tiered feminine pad, constructed for successive removal of the pads, the middle pad is smaller with edges located inwardly of the edges of the first and second layer.

US 2009/0287171 discloses a layered absorbent product constructed for successive removal of the layers. Temporal adhesive is provided along the edges and a gap is formed in an adhesive-free portion.

WO 95/29655 discloses a product in which the first layers are longer than the lower layers in order to provide grip portions extending outside the layers beneath.

In view of the above solutions there still exists a need to facilitate the successive removal of the absorbent articles made up of more than one stacked absorbent pad. There is furthermore still a need for absorbent articles made up of more than one stacked absorbent pad which may be manufactured by a simple manufacturing process.

SUMMARY

It is desired to fulfill the above mentioned need and to provide a disposable absorbent article including more than one stacked absorbent pad which exhibits facilitated means for successive removal of the stacked pads and which absorbent article does not require a complex manufacturing process.

The above can be achieved by an absorbent article and the methods of producing the absorbent article according to the appended claims.

Thus, in one aspect, an absorbent article including at least two stacked absorbent pads which are releasably attached to each other is provided. The absorbent article includes a first, user facing, absorbent pad and a second, garment facing, absorbent pad. Each of the absorbent pads includes a liquid permeable topsheet and a backsheet. The absorbent pads furthermore have lengths in a longitudinal direction and widths in a transverse direction. The absorbent pads each have first and second end regions and a central region therebetween as seen in the longitudinal direction. The absorbent pads further include first and second lateral edges extending in the longitudinal direction and first and second transverse edges extending in the transverse direction. The absorbent pads furthermore include first and second lateral margins extending along said first and second lateral edges, and first and second transverse margins extending along said first and second transverse edges. The first and second absorbent pads are releasably attached to each other by joints along at least part of the respective first and second lateral margins in at least one of the end regions. The first and second absorbent pads are furthermore unattached from each other in an unattached region along at least a part of the transverse margins in the end region including the joints along the lateral margins. The first absorbent pad has a greater width, at least between the joints along the lateral margins in the end region, than the second absorbent pad, causing the first absorbent pad to bulge and form a finger lift between the first and second absorbent pads at the unattached region.

The bulging finger lift makes the removal of the first absorbent pad from the second absorbent pad simple and convenient and the contact with the soiled first absorbent pad is minimized for the user's fingers during removal.

In one aspect the first absorbent pad is at least about 5 mm wider than the second sanitary article between the joints, or between about 5 mm and about 10 mm wider than the second sanitary article between the joints. This can ensure that the first absorbent pad will bulge properly and that a finger lift will be formed.

Advantageously, the unattached region at the first or second transverse margin is at least about 10 mm in the transverse direction. The unattached region may also extend along essentially the entire transverse margin.

In one embodiment, the absorbent pads are mutually attached by joints along the entire first and second lateral margins in an edge-to-edge relationship.

In one aspect, the first absorbent pad is wider than the second absorbent pad along the entire length of the pads.

In another aspect, the first and second absorbent pads have the same length as each other.

In one embodiment, the joints are made by means of adhesive, in another embodiment, the joints are made by means of embossing. In still another embodiment, the joints are made by means of ultrasound.

In one embodiment, the absorbent article is rectangular in shape. A rectangular shape decreases the material waste during the manufacturing process.

In one embodiment, the absorbent article has an hourglass shape.

In one embodiment, the absorbent pads are pantyliners.

A method for making the absorbent article in a cross-wise direction is also provided, including the steps of; advancing a first continuous web, including a liquid permeable topsheet and a backsheet permanently attached to each other, from a first assembly section at a first speed $V_1$; advancing a second continuous web, including a liquid permeable topsheet and a backsheet permanently attached to each other, from a second assembly section at a second speed $V_2$ which is lower than the first speed $V_1$. Bringing the first web and the second web together in a web-bonding means and mutually bonding the webs with releasable joints. As a result of the higher feeding speed $V_1$ of the first web in relation to the feeding speed $V_2$ of the second web, the first web will bulge upon entering the web-bonding means, whereas the second web remains essentially smooth. The final absorbent articles are then cut out in a cross-wise direction from the bonded webs.

In one embodiment, the bulging effect will be achieved by: advancing a first continuous web from a first assembly section onto a forming roll including a plurality of recesses extending in an axial direction on the web-contacting surface of the forming roll and conforming the first web to the recesses by applying suction or pressure against the first web. In parallel, advancing the second continuous web, from a second assembly section and bringing the first and second web together in a web-bonding means located on a level with or downstream from the forming roll. At the web-bonding means releasable joints are formed between the first and second webs. The, first web will bulge upon formation of the joints as a result of the conformation of the first web to the recesses in the formation roll while the second web will remain essentially smooth.

In one aspect, the recesses extending in an axial direction of the forming roll will extend throughout the entire width of the forming roll.

In one aspect, the speed $V_1$ is between about 5% and about 40% higher than the speed $V_2$, or between about 5% and about 30% higher or even between about 5% and about 20% higher.

A further method for making the absorbent article in a length-wise direction is also provided, including the steps of: advancing a first continuous web, including a liquid permeable topsheet and a backsheet permanently attached to each other, from a first assembly section onto a first rotating roller including a circumferential recess on the web-contacting surface of the roll and conforming the first web to the recess by applying suction or pressure against the first web. In parallel, advancing a second continuous web, including a liquid permeable topsheet and a backsheet permanently attached to each other, from a second assembly section and bringing the first and second web together in a web-bonding means located on a level with or downstream the forming roll. At the web-bonding means releasable joints are formed between the first and second web. The first web will bulge upon formation of the joints as a result of the conformation of the first web to the recesses in the formation roll while the second web will remain essentially smooth. The final absorbent articles are then cut out in a length-wise direction from the bonded webs.

In one aspect, the circumferential recess extends in the middle of the web-contacting surface of the forming roll.

In one embodiment, the joints between the first and second continuous webs are made by means of embossing, alternatively the joints are made by means of adhesive.

BRIEF DESCRIPTION OF THE DRAWINGS

Embodiments of the invention will be described in greater detail in the following by way of example only with reference to various non-limiting embodiments as depicted in the annexed drawings, in which.

DETAILED DESCRIPTION OF PARTICULAR EMBODIMENTS

Embodiments of the invention will be described in further detail in the following with reference to the drawings in which reference number 1 generally denotes an absorbent article including absorbent pads. The term "absorbent pad" refers to products that are placed against the skin of the wearer to absorb and contain body exudates, like urine, faeces and menstrual fluid. Embodiments of the invention refer to disposable absorbent pads, which means pads that are not intended to be laundered or otherwise restored or reused as absorbent pads after use. Examples of disposable absorbent pads include feminine hygiene products such as sanitary napkins, pantyliners, feminine inserts, incontinence pads, diaper inserts and the like.

Figure 1:
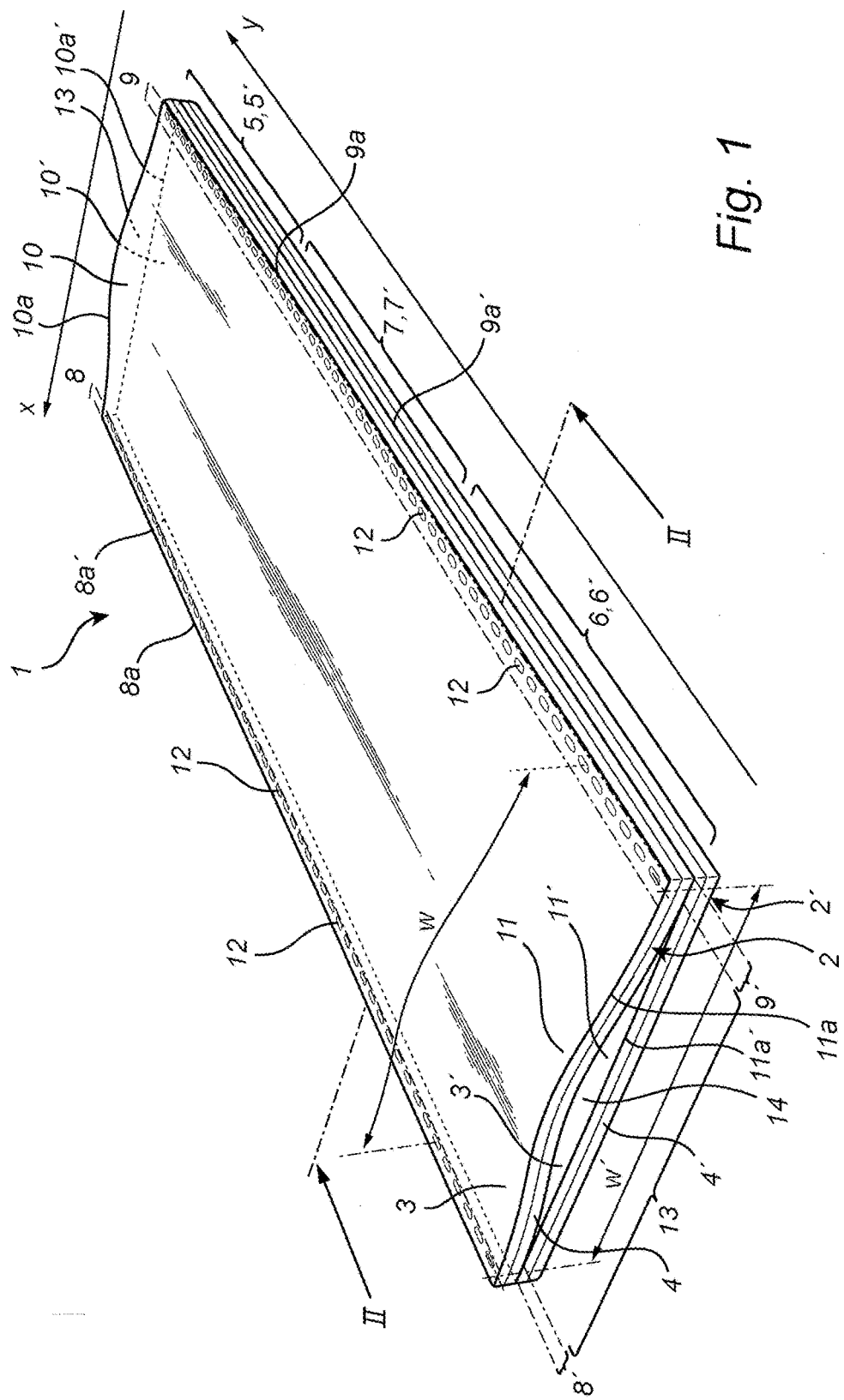
FIG. 1 is a perspective view of an absorbent article made up of more than one stacked absorbent pad according to one embodiment of the present invention.

With particular reference to FIG. 1, there is schematically shown an absorbent article 1 having a rectangular shape including two stacked absorbent pads, a first, user facing absorbent pad 2 and a second, garment facing, absorbent pad 2'. Each of the absorbent pads 2,2' includes a liquid permeable topsheet 3,3' and a backsheet 4,4'. The absorbent article 1 may of course be made up of more than two stacked absorbent pads, such as a third and a fourth absorbent pad. The second absorbent pad 2' should then have a greater width w' than the third absorbent pad and the third absorbent pad should have greater width than the fourth absorbent pad. That is, if a bulging effect and a finger lift 14 is desired between each of the absorbent pads.

The absorbent article extends in a longitudinal direction Y and in a transverse direction X, and each of the stacked absorbent pads making up the absorbent article has a first 5,5' and a second 6,6' end region and a central region 7,7' therebetween as seen in the longitudinal direction Y. The absorbent pads further include first lateral edges 8a,8a' and second lateral edges 9a,9a' extending in the longitudinal direction Y and first transverse edges 10a,10a' and second transverse edges 11a,11a' extending in the transverse direction X. The absorbent pads further include first lateral margins 8,8' and second lateral margins 9,9' extending along the lateral edges 8a,8a',9a,9a' and first transverse margins 10,10' and second transverse margins 11,11' extending along the transverse edges 10a,10a',11a,11a'. By "margin" is meant the area immediately adjacent to the edge, the area being not more than about 1 cm from the edge. The first and second absorbent pad 2,2' are releasably attached to each other by embossed joints 12 extending along the first 8,8' and the second 9,9' lateral margins. By "joint" is meant a continuous or discontinuous attachment between elements or components. The joints may be made by for example embossing, adhesive or ultrasound. By "releasably attached" or "releasable joints" or derivatives thereof is meant that elements are attached by joints that permit their separation substantially without causing the tearing, breaking or destruction of those elements or components According to FIG. 1, the first 2 and second 2' absorbent pads are furthermore unattached from each other along the transverse margins 10,10',11,11' in an unattached region 13. The width w of the first absorbent pad 2 is between about 5 and about 30 mm greater along the entire lengths of the absorbent pads 2,2' than the width w' of the second absorbent pad 2'. Due to the greater width w of the first absorbent pad 2 between the joints 12 along the first and second lateral margins 8,8',9,9' the first absorbent pad 2 will bulge forming a finger lift 14 between the first and second absorbent pads along the transverse margins 10,10',11,11'. The "width" being measured along the surface of the absorbent pad 2 in a flat position, which may be achieved by detaching the first absorbent pad 2 from the second absorbent pad 2'.

The joints 12 do not need to be present along the entire lengths of the lateral margins 8,8',9,9' in order to achieve the bulging effect defining the finger lift 14 between the first and the second absorbent pad 2,2' at the unattached region 13, but at least along the first or second end region 5,5' or 6,6' as long as the width w of the first absorbent pad 2, between the joints 12, is greater than the width w' of the second absorbent pad 2', and that the transverse margin 10,10' or 11,11' in this end region 5,5' or 6,6' is left unattached.

The stacked absorbent pads 2,2' may be substantially rectangular in shape. This shape reduces the material waste during the cutting step in the manufacturing process. The stacked absorbent pads 2,2' may also have the shape of an hourglass, with a slightly reduced width w,w' in the central region 7,7'. When the absorbent article 1 has the hourglass shape, the first absorbent pad 2 should especially be wider than the second absorbent pad 2' at the widest point of the second absorbent pad 2' in either the first or second end region 5,5' or 6,6'.

Figure 2:
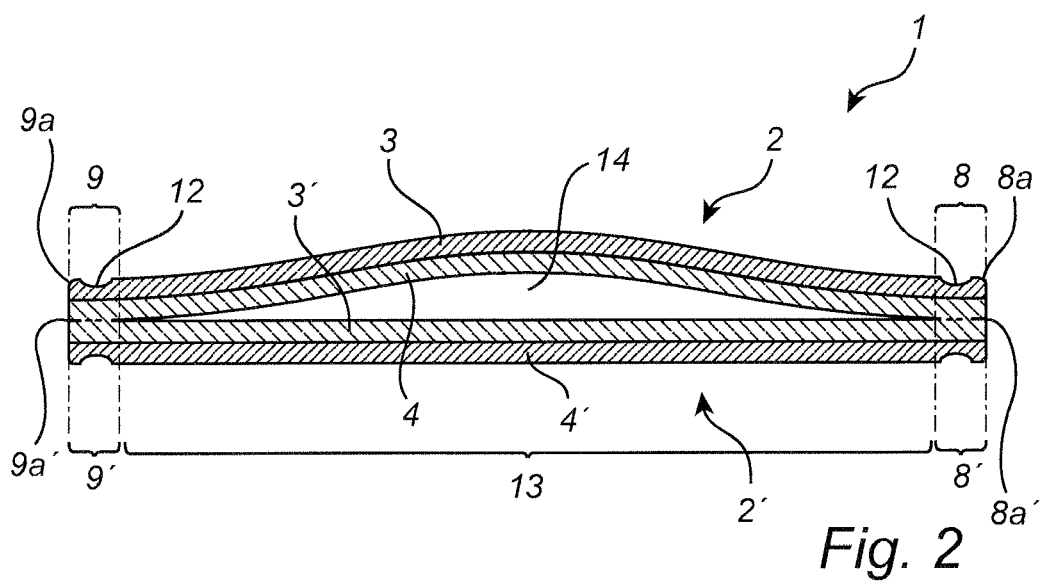
FIG. 2 is a cross-sectional view through the absorbent article according to the line II-II in FIG. 1.

FIG. 2 is a cross-sectional view through the absorbent article according to FIG. 1.

Figure 3:
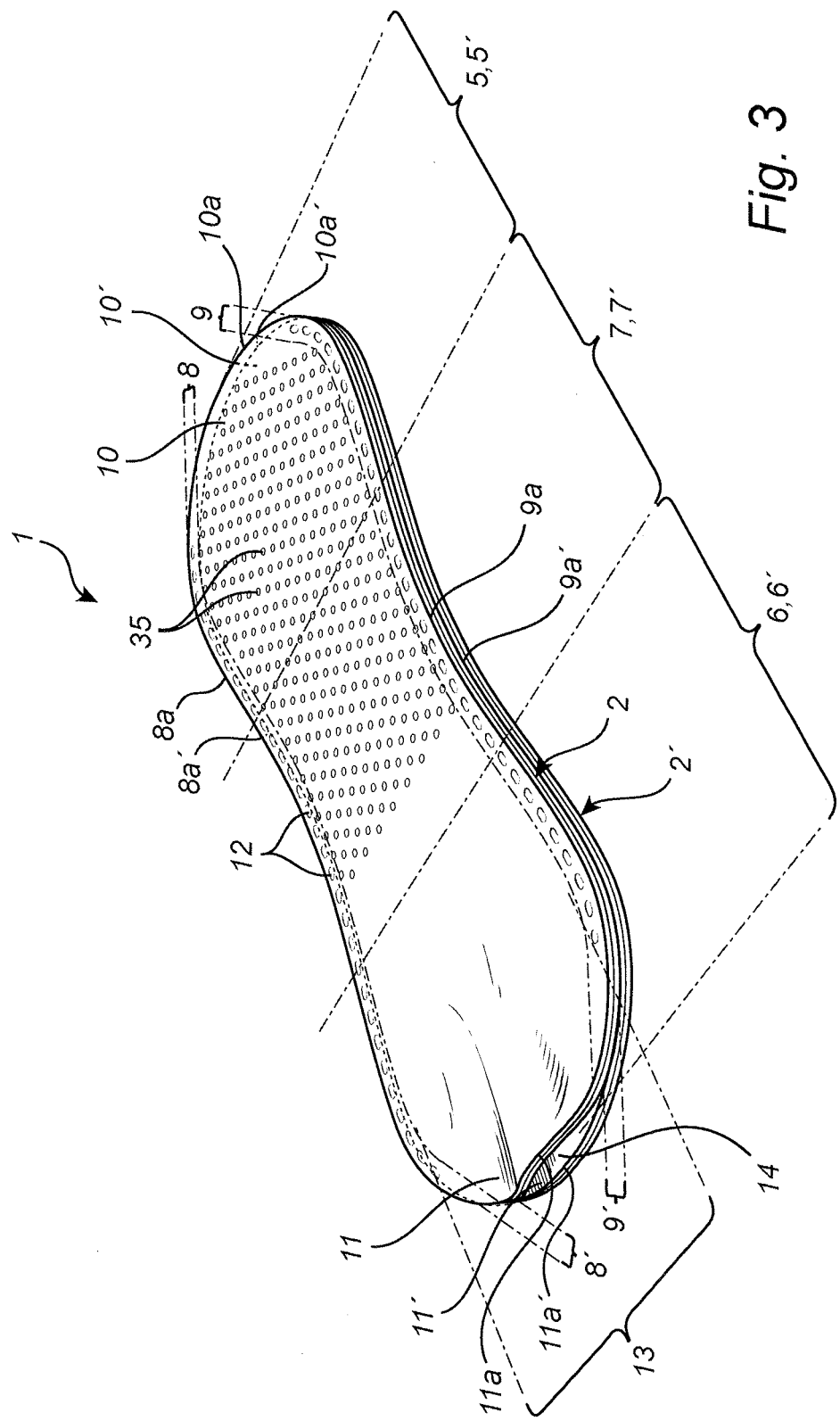
FIG. 3 is a perspective view of an absorbent article made up of more than one stacked absorbent pad according to an alternative embodiment of the present invention.

FIG. 3 shows an absorbent article 1 having an hourglass shape with the lateral margins 8,8',9,9' of the first 2 and second 2' absorbent pads attached by embossed joints 12, and the second transverse margins 11,11' are left unattached. The first end regions 5,5' and part of the central region 7,7' are furthermore attached by evenly spread embossed dots 35 in order to keep the first absorbent pad 2 essentially flat in the first end region. Alternatively, the embossed dots may also be in the form of decorative patterns and adhesive or ultrasound may also be used to bond together the first and second absorbent pads 2,2' and form the joints 12 and/or dots. To have the bulging effect only in the second end region 6,6', being the rear end region during use by a wearer, would give an anatomically shaped product with good fit.

The following is a description of the different components of the absorbent pad.

Topsheet

The liquid permeable topsheet 3,3' can include a nonwoven material, e.g. spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose, etc. or from a mixture of natural and manmade fibres. The topsheet material may further be composed of tow fibres, which may be bonded to each other in a bonding pattern, as e.g., disclosed in EP-A-1 035 818. Further examples of topsheet materials are porous foams, apertured plastic films, etc. The materials suited as topsheet materials should be soft and non-irritating to the skin and intended to be readily penetrated by body fluid, e.g., urine or menstrual fluid. The topsheet may be different in different parts of the absorbent article.

Backsheet

The backsheet 4,4' includes a liquid impervious material, such as a thin plastic film, e.g., a polyethylene or polypropylene film, a nonwoven material coated with a liquid impervious material, a hydrophobic nonwoven material, which resists liquid penetration, or a laminate including plastic films and nonwoven materials. The liquid impervious backsheet material 4,4' may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens.

Absorbent Core

The absorbent core can be of any conventional kind. Examples of commonly occurring absorbent materials are cellulosic fluff pulp, tissue layers, highly absorbent polymers called superabsorbents, absorbent foam materials, absorbent nonwoven materials or the like. It is common to combine cellulosic fluff pulp with superabsorbent polymers in an absorbent core. Superabsorbent polymers are waterswellable, water-insoluble organic or inorganic materials capable of absorbing at least about 20 times their weight in an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers may be lightly crosslinked to render the material substantially water insoluble. Suitable superabsorbent materials are further surface crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like.

A high absorption capacity is provided by the use of high amounts of superabsorbent material. For an absorbent core including a matrix of hydrophilic fibers, such as cellulosic fibers, and superabsorbent material, the proportion of superabsorbent material may be between about 10% and about 90% by weight, or between about 30% and about 70% by weight.

It is conventional in absorbent articles to have absorbent cores including layers of different properties with respect to liquid receiving capacity, liquid distribution capacity and storage capacity. The thin absorbent bodies, which are common in for example baby diapers and incontinence guards, often include a compressed mixed or layered structure of cellulosic fluff pulp and superabsorbent polymers. The size and absorbent capacity of the absorbent core may be varied to be suited for different uses such as for infants or for adult incontinent persons.

The absorbent core may further include an acquisition distribution layer placed on top of the primary absorbent body and which is adapted to quickly receive and temporarily store discharged liquid before it is absorbed by the primary absorbent core. Such acquisition distribution layers may be composed of porous fibrous waddings or foam materials.

A process of making the disposable absorbent article according to claim 1 in a cross-wise direction includes the steps of advancing a first continuous web 15, including a liquid permeable topsheet web 30 and a backsheet web 40 permanently attached to each other, from a first web assembly section 16 at a first speed $V_1$. From a second web assembly section 16' at a second speed $V_2$ which is lower than the first speed $V_1$, advancing a second continuous web 15', including a liquid permeable topsheet web 30' and the backsheet web 40' permanently attached to each other. The first and second continuous webs 15,15' may of course also include further components such as absorbent cores and/or acquisition layers between the topsheet and backsheet webs. The speed of the first continuous web 15 will thus be higher than the speed of the second continuous web 15' as the two webs move towards the web-bonding means 18. The web-bonding means includes an ultrasonic horn and a rotating counter-pressure roll whose peripheral speed corresponds to the first speed $V_1$. Alternatively, the web-bonding-means may also include an embossing roll or adhesive. The ultrasonic horn and the counter-pressure roll defines there between a nip through which the two webs 15,15' pass. The first web 15 will pass between the horn and the second web 15' will lie against the rotating counter-pressure roll. As the speed of the first continuous web 15 is higher than the speed of the second continuous web 15' when passing through the web-bonding means 18 and higher than the speed with which the assembly 23 of the first and second web 15,15' leaves the web-bonding means 18 the first web will bulge. This is a result of the sudden transition from the higher speed $V_1$ upstream of the web-bonding moment, to the lower speed $V_2$ downstream of the web-bonding moment. This will result in the formation of cross-wise bulges in the first continuous web 15. These bulges are permanently locked between the joints 12 formed by the web-bonding means 18 and will define the finger lift 14 in the final absorbent article. The joints 12 may be formed as parallel lines, or dotted lines, extending in a cross-wise direction at locations which are to form the lateral margins 8,8',9,9' of the absorbent pads 2,2' after cutting the assembly 23 to form the final absorbent article 1. The absorbent articles 1 are cut out by a cutting cylinder in a cross-wise direction.

Figure 4:
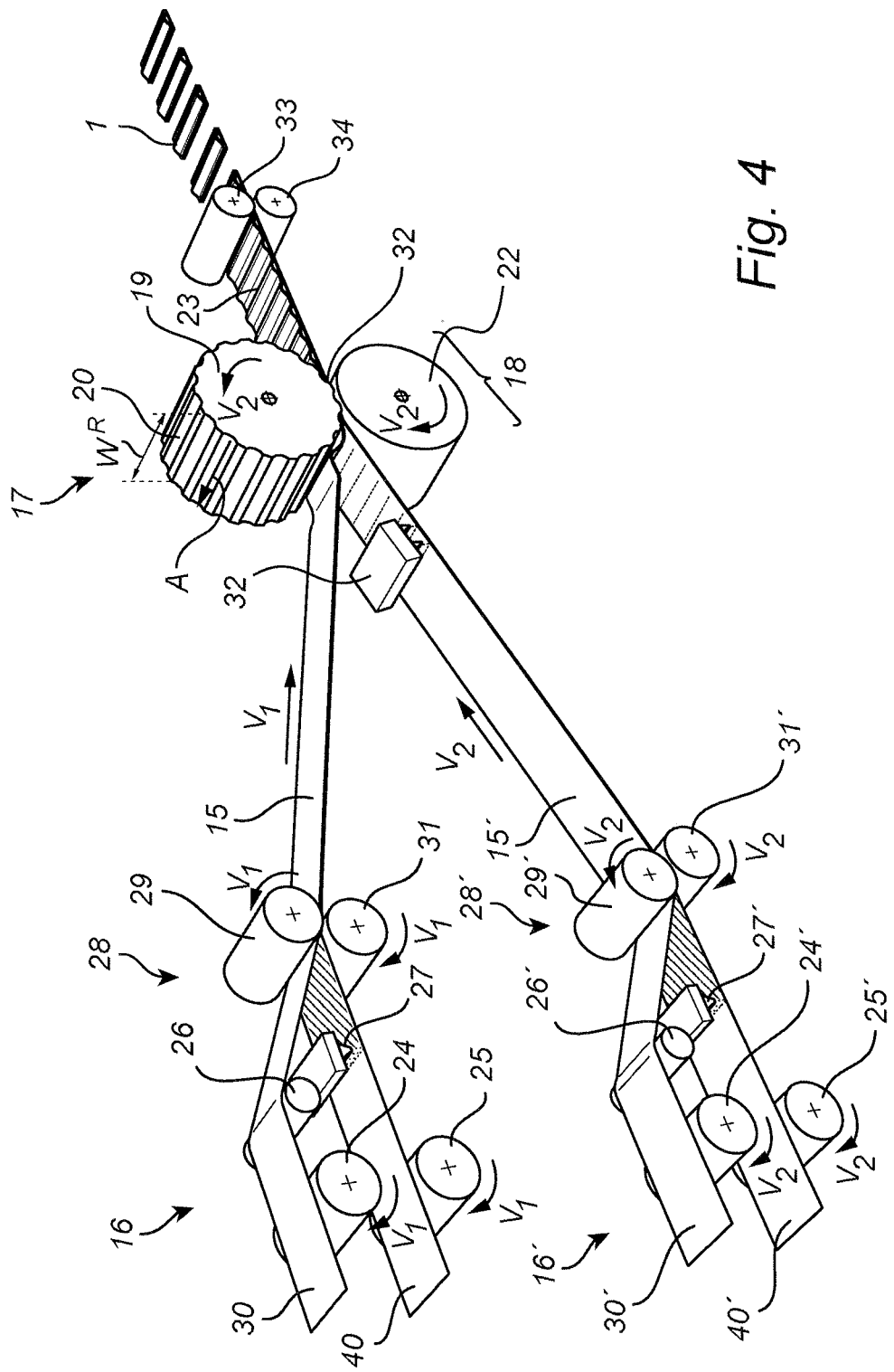
FIG. 4 illustrates schematically a method and an arrangement according to one embodiment of the invention.

FIG. 4 is a schematic diagram exemplarily illustrating a method of making the absorbent article 1 in a cross-wise direction. The method includes a first web assembly section 16 for making the first continuous web 15 forming the first absorbent pads 2, a second web assembly section 16' for making the second continuous web 15' forming the second absorbent pads 2' and a third forming and assembly section 17 provided downstream of the first and second sections 16,16' to obtain the finished absorbent article 1.

The first and second sections 16,16' both represent a method for assembling a simple absorbent pad including only a topsheet and a backsheet. The absorbent pad may of course also include an acquisition layer and/or an absorbent core. In the first web assembly section 16 the topsheet web 30 and the backsheet web 40 are continuously fed from feed rolls 24,25 whose peripheral speeds are equal to a first speed $V_1$, towards the joining section 28. In the second section 16' the topsheet web 30' and the backsheet web 40' are continuously fed from feed rolls 24',25' whose peripheral speed is equal to a second speed $V_2$, towards the joining section 28'. The continuous topsheet webs 30,30' are first fed towards adhesive applying sections 27,27' where spray adhesive is applied onto the topsheet facing sides of the respective backsheet webs 40,40'. Alternatively, the adhesive applied to the continuous backsheet webs may be substituted by spot adhesive, intermittent line adhesive, spiral adhesive or any other known method. The joining sections 28 make permanent attachments between the continuous topsheet webs 30 and the continuous backsheet webs 40 by pressing the webs together between rotating pressure rolls 29 and 31 to make a first continuous web 15 and the joining section 28' make permanent attachments between the continuous topsheet webs 30' and the continuous backsheet webs 40' by pressing the webs together between rotating pressure rolls 29' and 31' to make a second continuous web 15'.

In the third forming and assembling section 17, the first and second continuous webs 15,15' are advanced downstream by means of, e.g., vacuum drive conveyor or guide rollers (not shown). The first continuous web 15 is advanced by the first speed $V_1$. The second continuous web 15' is advanced by the second speed $V_2$. The first speed $V_1$ is higher than that of the second speed $V_2$ and the speed of the first web 15 will thus be higher than the second web 16 as the two webs are fed towards the web-bonding means 18. The width of the final absorbent article 1 and the desired difference in width between the first and the second absorbent pads 2,2' determine the difference between the first speed $V_1$ and the second speed $V_2$. For example, if the absorbent article 1 has a width of 10 cm and the difference in width of the first and the second absorbent pads is 1 cm, i.e. the width of the first absorbent pad 2 is 11 cm and the width of the second absorbent pad 2' is 10 cm, the first speed $V_1$ should be 10% higher than the second speed $V_2$. The first web 15 is further advanced onto a rotating forming roll 19 whose peripheral speed is equal to the second speed $V_2$, leading to the first web 15 being slowed down and relaxed before advancing onto the forming roll 19. The rotating forming roll 19 includes a plurality of parallel recesses 20 extending in an axial direction (A) on the web-contacting surface throughout the entire width $w^R$ of the forming roll 19. The first web 15 is conformed to the recesses 20 by applying suction by vacuum against the first web 15 and parallel bulges will be formed in a cross-wise direction of the first web 15 when advancing from the forming roll 19. Alternatively, the first web 15 may be conformed to the recesses 20 by means of pressure from a rotating counter roller having a number of protruding elements disposed thereon. Advancing towards the web-bonding means 18 the second continuous web 15' passes an adhesive applying section 32 where lines of adhesive extending in a cross-wise direction are applied to the second continuous web 15' with a distance between each line of adhesive in the length-wise direction which exceeds the width of the recesses 20 and which does not exceed the imaginary width of the second absorbent pad 2', so that the absorbent first and second webs 15,15' are attached along the imaginary lateral margins 8,8',9,9' of the absorbent pads 2,2'. A suitable type of adhesive to use for attaching the first 2 and second 2' absorbent pad to each other is a pressure-sensitive hotmelt adhesive which has a very high self-adhesion but which can be readily separated from other materials, an example of such an adhesive is Luna tack® BD19, available from H.B. Fuller. The web bonding step for bonding the first and the second web 15,15' together includes the forming roll 19 and a rotating counter-pressure roll 22 whose peripheral speed is equal to the second speed $V_2$. The counter-pressure roll 22 and the forming roll 19 define therebetween a nip 32 through which the two webs 15,15' pass. The first web 15 will lie against the forming roll 19 and in the recesses 20 and the second web 15' will lie against the rotating counter pressure roll 22 as the two webs 15,15' are mutually bonded to form an assembly 23. The two webs 15,15' are pressed together and mutually bonded along the lines of adhesive which are located so that the two webs 15,15' bond at each side of the recess 20 when passing through the nip 32. Alternatively, the first and the second web 15,15' may also be assembled by other mechanical means such as by embossing. As the first and second webs 15,15' are mutually bonded together the bulges formed on the first web 15 from the forming roll 19 are permanently locked between lines of adhesive forming joints 12 along each side of the bulges which will define the finger grip in the final absorbent article 1. The assembly of the first and second web 24 is then cut by cutting cylinders 34,35 in cross-wise direction into absorbent articles 1.

Figure 5:
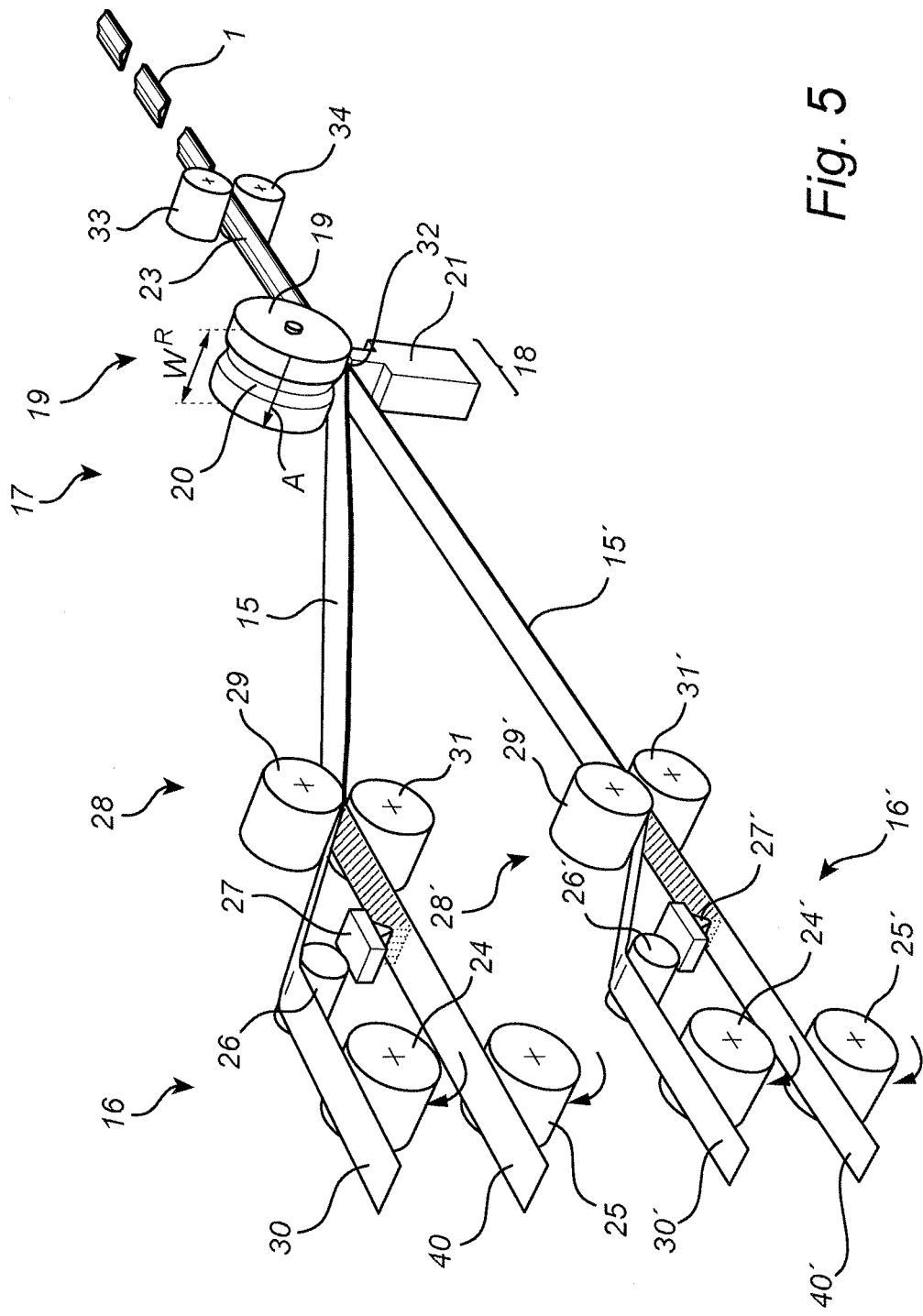
FIG. 5 illustrates schematically a method and an arrangement according to an alternative embodiment of the invention.

FIG. 5 is a schematic diagram exemplarily illustrating a further process of making the absorbent article 1. This process differs inter alia from the process described in FIG. 4 in that the absorbent articles are produced in length-wise direction. The process includes a first assembly section 16 for making the first continuous 15 web forming the first absorbent pads 2, a second assembly section 16' making the second continuous web 15' forming the second absorbent pads 2' and a third forming and assembly section 17 provided downstream of the first and second sections to obtain the finished absorbent articles 1.

In the first and second section, the topsheet web 30,30' and the backsheet web 40,40' are continuously fed from feed rolls 24,24' and 25,25' towards the joining section 28,28'. The continuous backsheet webs 40,40' are fed towards adhesive applying sections 27,27' where spray adhesive is applied onto the topsheet facing sides of the respective backsheet webs 40,40'. Alternatively, the adhesive applied to the continuous backsheet webs may be substituted by spot adhesive, intermittent adhesive, spiral adhesive or any other known method. The joining sections 28,28' make permanent attachments between the continuous topsheet webs 30 and the continuous backsheet webs 40 and between the continuous topsheet webs 30' and the continuous backsheet webs 40' by pressing the webs together between rotating pressure rolls 29,31 and 29',31' respectively to make first and second continuous webs 15,15'.

In the third forming and assembly section 17 of FIG. 5, the first and second continuous webs 15,15' are advanced downstream by means of e.g., vacuum drive conveyer or guide rollers (not shown). The first continuous web 15 is advanced onto a forming roll 19 including a continuous centered circumferential recess 20 on the web-contacting surface of the roll 19. The first web 15 is conformed to the recess 20 by applying suction or pressure against the first web 15. As a result of the conformation, the first web 15 will bulge in a length-wise direction when advancing from the forming roll 19 and when entering the subsequent web-bonding means 18. Alternatively, the first web may be conformed to the recess by means of pressure from a rotating counter roll having a centered circumferentially placed protruding forming element. The first web 15 may have a greater width than the second web 15' corresponding to the final difference in width between the first and second absorbent pad 2,2'. The forming roll 19 will function as a counter-pressure roll and will together with an ultrasonic horn 21 constitute the web-bonding means 18 which mutually attach the first and second continuous webs 15,15' to form an assembly 23. The first and second webs 15,15' are thus brought together in the web-bonding means 18. The forming roll 19 and the ultrasonic horn 21 define therebetween a nip 32 through which the two webs 15,15' pass. The first web 15 will lie against the forming roll 19 and the second web 15' will pass between the ultrasonic horn 21 as the two webs 15,15' are mutually bonded to form the assembly 23. The ultrasonic horn 21 will form welded dots forming lines in a length-wise direction at each side of the bulges formed, along the imaginary lateral margins 8,8',9,9' of the absorbent pads 2,2'. Alternatively, the first and second webs 15,15' may also be assembled by other mechanical means such as embossing. As the first and second webs 15,15' are mutually welded, the bulges formed on the first web 15 from the forming roll 20 are permanently locked between the joints 12 formed along each side of the bulges. The assembly 23 of the first and second web is then cut by cutting cylinders 33,34 in length wise direction into absorbent articles 1. If the first and second webs 15,15' have equal widths the assembly 23 may be cut along the lateral edges 8a,8a',9a,9a' as well so as to give the absorbent pads 2,2' an edge-to-edge relationship and/or to shape the absorbent article .

The invention claimed is:
1. A disposable absorbent article comprising at least two stacked absorbent pads releasably attached to each other, including a first, user facing, absorbent pad and a second, garment facing, absorbent pad,
   wherein each absorbent pad includes:
      a liquid permeable topsheet;
      a backsheet;
      a length in a longitudinal direction and a width in a transverse direction;
      a first end region, a second end region, and a central region therebetween as seen in the longitudinal direction;
      a first lateral edge and a second lateral edge extending in said longitudinal direction;
      a first transverse edge and a second transverse edge extending in said transverse direction;
      a first lateral margin and a second lateral margin extending along said first and second lateral edges; and
      a first transverse margin and a second transverse margin extending along said first and second transverse edges,
   wherein said first and second absorbent pads are releasably attached to each other by joints along at least part of said first lateral margin and said second lateral margin, respectively, in at least one of said end regions, said joints being located substantially the same distance from said first lateral edge and said second lateral edge of each of said first and second absorbent pads, wherein said first absorbent pad and said second absorbent pad are unattached from each other in an unattached region along at least a part of said first transverse margins and said second transverse margins in said end region comprising said joints along said first lateral margins and said second lateral margins, wherein said width of said first absorbent pad between said joints is greater than said width of said second absorbent pad between said joints and said first absorbent pad and said second absorbent pad are arranged so that said first absorbent pad will bulge forming a finger lift between said first absorbent pad and said second absorbent pad at said unattached region.

2. The disposable absorbent article according to claim 1, wherein said width of said first absorbent pad is at least 5 mm greater than said width of said second absorbent pad between said joints.

3. The disposable absorbent article according to claim 1, wherein said width of said first absorbent pad is at least 10 mm greater than said width of said second absorbent pad between said joints.

4. The disposable absorbent article according to claim 1, wherein said unattached region at said first transverse margins or said second transverse margins is at least 10 mm in the transverse direction.

5. The disposable absorbent article according to claim 1, wherein said first absorbent pad and said second absorbent pad are attached to each other by joints along entire lengths of said first lateral margins and said second lateral margins in an edge-to-edge relationship.

6. The disposable absorbent article according to claim 1, wherein said width of said first absorbent pad is greater than said width of said second absorbent pad along entire lengths of said absorbent pads.

7. The disposable absorbent article according to claim 1, wherein said first absorbent pad and said second absorbent pad have the same length.

8. The disposable absorbent article according to claim 1, wherein, for each of said absorbent pads, the lengths of each of said first end region, said second end region, and said central region is a third of the length of said absorbent pad.

9. The disposable absorbent article according to claim 1, wherein the joints are made by adhesive.

10. The disposable absorbent article according to claim 1, wherein the joints are made by embossing.

11. The disposable absorbent article according to claim 1, wherein said absorbent article is rectangular in shape.

12. The disposable absorbent article according to claim 1, wherein said absorbent pads are pantyliners.

13. A method of producing the disposable absorbent article according to claim 1, comprising:
advancing a first continuous web, which includes the liquid permeable topsheet and the backsheet permanently attached to each other, from a first assembly section at a first speed;
advancing a second continuous web, which includes the liquid permeable topsheet and the backsheet permanently attached to each other, from a second assembly section at a second speed, which is lower than the first speed;
bringing said first and second continuous web together in a web-bonding section and forming releasable joints between said first and second continuous web;
advancing the bonded webs from the web-bonding section at a speed which is equal to the second and lower speed,
wherein the first continuous web will bulge upon formation of said joints as a result of the higher feeding speed of the first continuous web in relation to the second continuous web, whereas the second continuous web remains essentially smooth; and
cutting out in a cross-wise direction the disposable absorbent articles comprising the stacked absorbent pads from the bonded webs.

14. The method article according to claim 13, wherein the step of advancing said first continuous web further includes advancing said first continuous web from said first assembly section onto a forming roll having a width extending in an axial direction of said forming roll, said forming roll comprising a plurality of recesses extending in said axial direction on the web-contacting surface of said roll and conforming said first continuous web to said recesses by applying suction or pressure against said first web, and;
wherein the web-bonding section is located on a level with or downstream of said forming roll such that the first web will bulge upon formation of said joints as a result of said conformation of the first web to said recess, whereas the second web remains essentially smooth.

15. The method according to claim 14, wherein said recesses extend throughout the entire width of said forming roll.

16. A method of producing the absorbent article according to claim 1, comprising:
advancing a first continuous web, which comprises said liquid permeable topsheet and said backsheet permanently attached to each other, from a first assembly section onto a forming roll comprising a circumferential recess on the web-contacting surface of said forming roll and conforming said first continuous web to the circumferential recess by applying suction or pressure against said first continuous web;
advancing a second continuous web, comprising said liquid permeable topsheet and said backsheet permanently attached to each other, from a second assembly section;
bringing said first and second continuous web together in a web-bonding section located on a level with or downstream of said forming roll and forming releasable joints between said first and second continuous web at said web-bonding section, wherein the first continuous web will bulge during formation of said joints as a result of said conformation of the first continuous web to said recess, whereas the second continuous web remains essentially smooth; and
cutting out in a length wise direction the disposable absorbent articles comprising the stacked absorbent pads from the bonded webs.

17. The method according to claim 16, wherein said circumferential recess extends in the middle of the web-contacting surface of said forming roll.

18. The method according to claim 13, wherein the joints between said first and second continuous webs are made by embossing or by ultrasound.

19. The method according to claim 13, wherein the joints between said first and second continuous webs are made by of adhesive.

20. The method according to claim 13, wherein said first speed is at least between 5% and 40% higher than said second speed.

* * * * *